(12) United States Patent
Park et al.

(10) Patent No.: US 7,229,794 B2
(45) Date of Patent: Jun. 12, 2007

(54) MICROORGANISM PRODUCING L-THREONINE HAVING INACTIVATED GALR GENE, METHOD OF PRODUCING THE SAME AND METHOD OF PRODUCING L-THREONINE USING THE MICROORGANISM

(75) Inventors: Young Hoon Park, Seongnam (KR); Byoung Choon Lee, Seoul (KR); Kwang Myung Cho, Icheon (KR); Dae Cheol Kim, Suwon (KR); Yong Uk Shin, Seoul (KR); Jin Ho Lee, Icheon (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 11/049,845

(22) Filed: Feb. 4, 2005

(65) Prior Publication Data

US 2005/0176114 A1    Aug. 11, 2005

(30) Foreign Application Priority Data

Feb. 5, 2004    (KR) .................... 10-2004-0007529

(51) Int. Cl.
*C12P 1/00* (2006.01)
*C12P 21/04* (2006.01)

(52) U.S. Cl. .................... 435/71.2; 435/41; 435/45; 435/71.1

(58) Field of Classification Search .................... None
See application file for complete search history.

(56) References Cited

FOREIGN PATENT DOCUMENTS

| KR | 9208365 B | 9/1992 |
|---|---|---|
| WO | WO 96/34961 A1 | 11/1996 |
| WO | WO 2004/087937 A1 | 10/2004 |

OTHER PUBLICATIONS

Cummings L, Riley L, Black L, Souvorov A, Resenchuk S, Dondoshansky I, Tatusova T. Genomic BLAST: custom-defined virtual databases for complete and unfinished genomes. FEMS Microbiol Lett. Nov. 5, 2002;216(2):133-8.*

NCBI genomic BLAST with microbial genomes pp. 1-11.*

Mims et al., Medical Microbiology Third EditionElsevier Science, 2004, pp. 280-282.*

Ajdic D, Ferretti JJ.Regulation of the galactose operon of *Streptococcus mutans*. Adv Exp Med Biol. 1997;418:1015-8. PMID: 9331823 (Abstract).*

Tokeson JP, Garges S, Adhya S. Further inducibility of a constitutive system: ultrainduction of the gal operon.J Bacteriol. Apr. 1991;173(7):2319-27.*

Hernandez-Montalvo, V. et al., "Expression of *galP* and *glk* in a *Escherichia coli* PTS Mutant Restores Glucose Transport and Increases Glycolytic Flux to Fermentation Products," *Biotechnology and Bioengineering*, 83(6):687-694, (Sep. 2003).

Tokeson, J.P.E., et al., "Further Inducibility of a Constitutive System: Ultrainduction of the *gal* Operon," *J. Bacteriology*, 173(7):2319-2327, (Apr. 1991).

V. Hernandez-Montalvo et al., "Characterization of Sugar Mixtures Utilization by an *Escherichia coli* Mutant Devoid of the Phosphotransferase System," *Appl. Microbiol. Biotechnol.*, 57:186-191 (2001).

M. Geanacopoulos et al., "Functional Characterization of Roles of GalR and GalS as Regulators of the *gal* Regulon," *J. Bacteriology*, 179(1):228-234, (Jan. 1997).

F.R. Blattner et al., "The Complete Genome Sequence of *Escherichia coli* K-12," *Science* 277:1453-1462 (1997).

G. Pozzi et al., "Competence for Genetic Transformation in Encapsulated Strains of *Streptococcus pneumoniae*: Two Allelic Variants of the Peptide Pheromone," *J. Bacteriology*, 178 (20): 6087-6090 (1996).

U. Güldener et al., "A New Efficient Gene Disruption Cassette For Repeated Use in Budding Yeast," *Nucleic Acids Research*, 24 (13):2519-2524 (1996).

Tokeson JPE, et al. "Further Inducibility of a Constitutive System Ultrainduction of the gal Operon," *Journal of Bacteriology* 1991, 173(7):2319-2327.

* cited by examiner

*Primary Examiner*—Joseph Woitach
*Assistant Examiner*—Maria Leavitt
(74) *Attorney, Agent, or Firm*—Rothwell, Figg, Ernst & Manbeck

(57) ABSTRACT

Provided are a microorganism capable of producing L-threonine and having an inactivated galR gene, a method of producing the same and a method of producing L-threonine using the microorganism. The microorganism can be used to produce L-threonine in high yield.

2 Claims, 2 Drawing Sheets

MICROORGANISM PRODUCING L-THREONINE HAVING INACTIVATED GALR GENE, METHOD OF PRODUCING THE SAME AND METHOD OF PRODUCING L-THREONINE USING THE MICROORGANISM

BACKGROUND OF THE INVENTION

This application claims the benefit of Korean Patent Application No. 10-2004-0007529, filed on Feb. 5, 2004, in the Korean Intellectual Property Office, the disclosure of which is incorporated herein in its entirety by reference.

FIELD OF THE INVENTION

The present invention relates to a microorganism having an inactivated galR gene, a method of producing the same and a method of producing L-threonine using the microorganism.

DESCRIPTION OF THE RELATED ART

L-threonine is an essential amino acid and is widely used as a feed and food additive, and also as a pharmaceutical and raw material for synthesizing some drugs. It has been produced by fermentation with artificial mutants of the genus *Escherichia, Coryneform bacteria, Seratia* and *Providencia*. For example, Japanese Patent Publication No. 10037/81 discloses a method of producing L-threonine using a strain belonging to the genus *Escherichia* which has a requirement for diaminopimelic acid and methionine, and has the resistance to the feedback inhibition by threonine of the biosynthetic system of threonine. Japanese Patent Application Laid-open No. 224684/83 discloses a method of producing L-threonine using a strain belonging to the genus *Brevibacterium* which is resistant to S-(2-aminoethyl)-L-cysteine and α-amino-β-hydroxy valeric acid and has a nutritional requirement for L-isoleucine and L-lysine. Korean Patent Application Laid-open No. 8022/87 discloses a method of producing L-threonine using a diaminopimelic acid and methionine-requiring, α-amino-β-hydroxy valeric acid-resistant strain belonging to the genus *Escherichia* which has an additional resistance to at least one substance selected from the group consisting of rifampicin, lysine, methionine, aspartic acid, and homoserine, or has a reduced ability to decompose L-threonine. Japanese Patent Application Laid-open No. 219582/90 discloses a method for producing L-threonine using a strain belonging to the genus *Providencia* which is resistant to α-amino-β-hydroxy valeric acid, L-ethionine, thiaisoleucine, oxythiamine, and sulfaguanidine, and has a requirement for L-leucine and also a leaky requirement for L-isoleucine.

However, the above known methods have the disadvantages that they fail to afford a high production of L-threonine or require costly requirements such as diaminopimelic acid and isoleucine. In other words, the use of diaminopimelic acid-requiring strains in the production of L-threonine includes an additional fermentation of diaminopimelic acid and thus may increase cost. Where a strain having a requirement for isoleucine is used for the production of L-threonine, costly isoleucine must be added to fermentation media, which increases cost.

In an attempt to overcome these disadvantages, the present inventors developed an L-threonine-producing strain of *Escherichia coli* which is resistant to L-methionine, L-threonine and L-lysine analogues and α-aminobutyric acid, and has a nutritional requirement for methionine and a leaky requirement for isoleucine. They successfully produced L-threonine by fermentation with the strain at higher yields than with prior strains. The strain and a method for producing L-threonine using said strain are disclosed in Korean Patent Publication No. 92-8365.

GalP protein is known as permease which transports various saccharides such as galactose and glucose to the inside of cells (see e.g. V. Hernandez-Montalvo F. Valle F. Bolivar G. Gosset, Appl Microbiol Biotechnol (2001) 57: 186-191). The GalR protein represses the expression of galP gene in cells (see e.g. MARK GEANACOPOULOS AND SANKAR ADHYA, JOURNAL OF BACTERIOLOGY, January 1997, p. 228-234, Vol. 179, No. 1).

The present inventors have intensively studied to select strains having an improved ability to produce L-threonine on the basis of conventional technologies and now discovered that L-threonine biosynthesis can be facilitated by inactivation of the galR gene.

SUMMARY OF THE INVENTION

The present invention provides a microorganism having an improved ability to produce L-threonine.

The present invention also provides a method of producing the microorganism.

The present invention also provides a method of efficiently producing L-threonine using the microorganism.

According to an aspect of the present invention, there is provided a microorganism capable of producing L-threonine and having an inactivated galR gene.

According to another aspect of the present invention, there is provided a method of producing a L-threonine-producing microorganisim, the method including: preparing an inactivated galR gene or a DNA fragment thereof; introducing the inactivated galR gene or the DNA fragment thereof into a microorganism capable of producing L-threonine to cause recombination with a galR gene present on a chromosome of the microorganism; and selecting microorganisms having an inactivated galR gene.

According to another aspect of the present invention, there is provided a method of producing L-threonine, the method including: culturing the microorganism as describe above; and isolating L-threonine from the culture.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
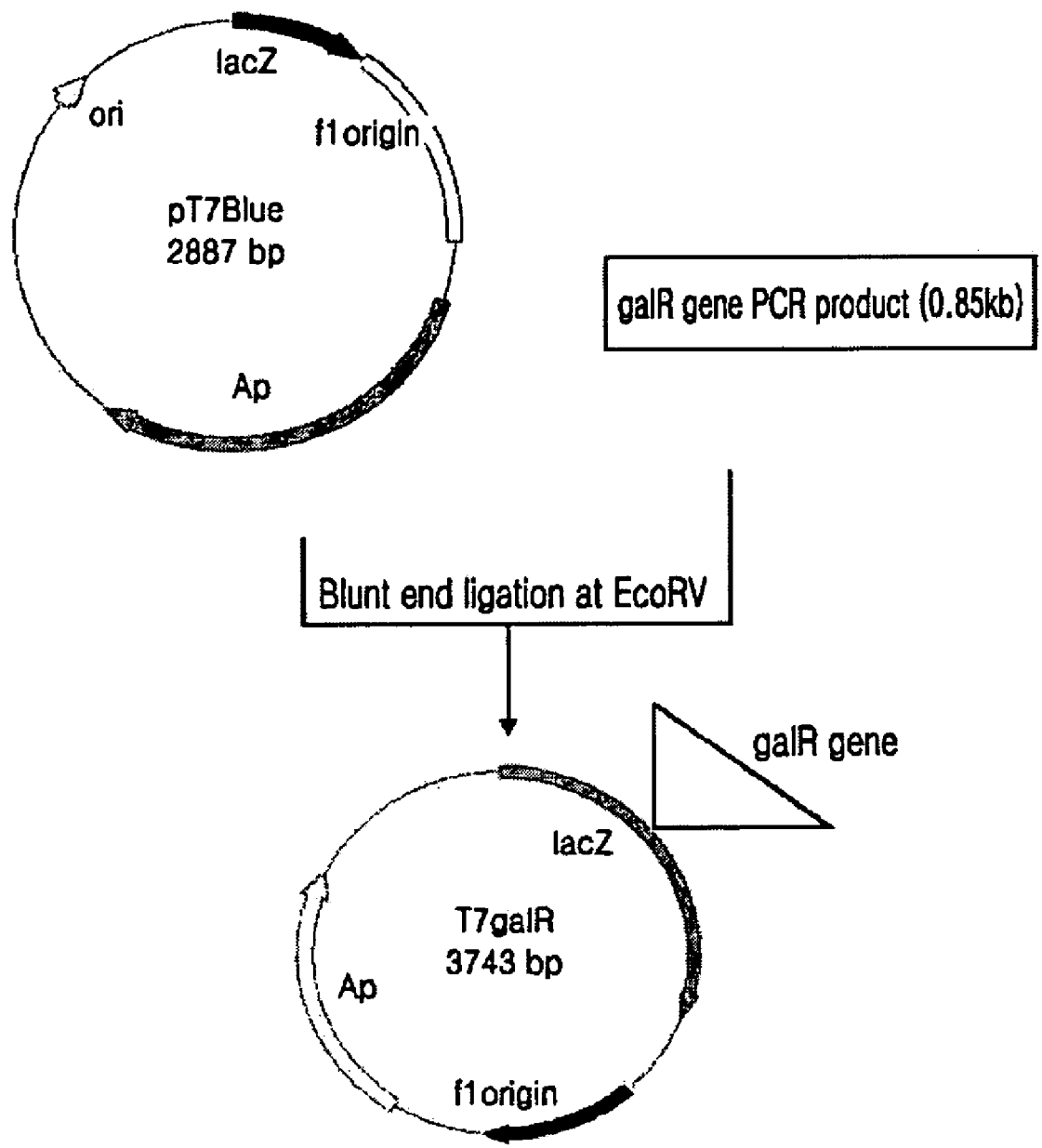
FIG. 1 depicts a construction of recombinant plasmid pTblue/galR including a galR gene.

The present invention provides a microorganism capable of producing L-threonine and having an inactivated galR gene.

In the present invention, the microorganism can produce L-threonine and includes prokaryotic and eukaryotic microorganisms having an inactivated galR gene. For example, strains belonging to the genus *Escherichia, Erwinia, Serratia, Providencia, Corynebacterium* and *Brevibacterium* can be included. Preferably, the microorganism belongs to the Enterobacteriaceae family and, more preferably, to the genus *Escherichia*. Most preferably, the microorganism is selected from the group consisting of *Echerichia coli* FTR2541 (KCCM-10539), *Echerichia coli* FTR2537 (KCCM-10540) and *Echerichia coli* FTR2533 (KCCM-10541).

Also, the microorganism may include L-threonine-producing mutants as well as natural microorganisms. Examples of the mutants include microorganisms belonging to L-threonine-producing *Escherichia coli* which are resistant to L-methionine, L-threonine and L-lysine analogues and α-aminobutyric acid, and have a nutritional requirement for methionine and a leaky requirement for isoleucine; and mutated microorganism in which at least one copy of phosphoenol pyruvate carboxylase (ppc) gene and thrA, thrB, and thrC genes contained in a threonine operon is further inserted in a chromosomal DNA, in addition to intrinsic ppc gene and genes in the threonine operon; microorganisms having an activated pckA gene which is involved in conversion of oxaloacetate (OAA), which is an intermediate for L-threonine biosynthesis, into phosphoenolpyruvate (PEP); mutated microorganisms having inactivated pckA gene and aspA gene which converts aspartate (Asp), which is another intermediate for L-threonine biosynthesis, into fumarate; and microorganisms having an inactivated tyrR gene which represses the expression of tyrB gene necessary for L-threonine biosynthesis. The L-methionine analogue may be at least one compound selected from the group consisting of D,L-ethionine, Norleucine, α-methyl-methionine and L-methionine-D,L-sulfoxymine. The L-threonine analogue may be at least one compound selected from the group consisting of α-amino-β-hydroxy valeric acid and D,L-threonine hydroxamate. The L-lysine analogue may be at least one compound selected from the group consisting of S-(2-aminoethyl)-L-cysteine and δ-methyl-L-lysine.

In the present invention, the galR protein represses the expression of galP gene encoding galactose permease which transports galactose to the inside of cells. For the *Escherichia coli*, the galR gene is known and can be obtained from genome sequence published by Blattner, et al. (Science 277: 1453-1462 (1997)) (Accession no. AAC75876). The genome sequence can also be obtained from National Center for Biotechnology Information (NCBI) in USA and DNA Data Bank of Japan (DDBJ). The galR gene also includes an allele generated by attenuation of genetic code or mutation.

The "inactivation" as used herein refers to no-expression of an active galR protein. Thus, the inactivation of the galR gene leads to an increase in expression of the galP gene.

The microorganism of the present invention can be produced by inactivating a galR gene present on a chromosome of a microorganism capable of producing L-threonine. The inactivation method may include causing mutation using light, such as UV-ray, or chemicals and isolating strains having an inactivated galR gene from the mutants. The inactivation method also includes a DNA recombination technology. The DNA recombination may be achieved, for example, by injecting a nucleotide sequence or vector including a nucleotide sequence with homology to the galR gene into the microorganism to cause homologous recombination. The nucleotide sequence and vector injected may include a dominant selectable marker.

The present invention also provides a method of producing a L-threonine-producing microorganisim, including: preparing an inactivated galR gene or DNA fragment thereof; introducing the inactivated galR gene or the DNA fragment thereof into a microorganism capable of producing L-threonine to cause recombination with a galR gene present on a chromosome of the microorganism; and selecting the microorganism having an inactivated galR gene.

The "inactivated galR gene or DNA fragment thereof" as used herein refers to a polynucleotide sequence which has a sequence homology to the galR gene in a host, but is not capable of expressing an active galR protein due to loss, displacement, and inversion. The introduction of the inactivated galR gene or DNA fragment thereof into a host cell can be achieved, for example, by transformation, conjugation, transduction or electroporation, but is not limited thereto.

When the inactivated galR gene or DNA fragment thereof is introduced into the host cell by transformation, the inactivation procedure can be carried out by mixing the polynucleotide sequence with a culture of the strain. While the strain is naturally competent for DNA uptake to be transformed, it is preferred that the strain can be previously rendered competent for DNA uptake by any suitable method (See e.g. LeBlanc et al., Plasmid 28, 130-145, 1992; Pozzi et al., J. Bacteriol. 178, 6087-6090, 1996). The inactivated galR gene or DNA fragment thereof has a foreign DNA piece introduced in a genome DNA fragment and replaces the wild-type chromosomal copy of the sequence with an inactivated state. In an embodiment of the present invention, the inactivated polynucleotide sequence includes "tails" comprising a part of the target site DNA at the 5' and 3' ends thereof. The tails should be at least 50 base pairs and preferably greater than 200 to 500 base pairs for efficient recombination and/or gene conversion. For convenience, the inactivated polynucleotide sequence can include a selectable marker, for example, an antibiotic resistance gene. Where the target DNA is disrupted with an antibiotic resistance gene, selection of transformants is carried out on agar plates containing suitable levels of an appropriate antibiotic. Following transformation, the inactivated polynucleotide sequence introduced into the host cell undergoes homologous recombination with the genomic DNA tails, resulting in inactivation of the wild-type genomic sequence. Inactivation recombination events are easily confirmed by, for example, Southern blotting, or more conveniently by polymerase chain reaction (PCR).

In an embodiment of the present invention, a method of producing the L-threonine-producing microorganism of the present invention comprises the following procedures.

First, genomic DNA is isolated from a strain that is capable of producing L-threonine and PCR is performed using it as a template by a conventional technology to amplify the galR gene.

Next, the obtained galR gene is cloned into a suitable plasmid or other vector. The recombinant vector is introduced by transduction into a host cell such as *E. coli*. After the transformant is grown and cells are isolated, the recombinant vector having galR genes is extracted. An antibiotic resistant gene fragment is then inserted into the galR gene of the extracted recombinant vector to form a recombinant vector having an activated galR gene. This recombinant vector is introduced by transformation into a host cell and the host cell is cultivated. Then, the propagated recombinant vector is isolated from the resultant transformant, and the polynucleotide sequence having an inactivated galR gene is obtained by suitable restriction enzyme digestion(s). Thereafter, this polynucleotide sequence is introduced into a host that is capable of producing L-threonine by a conventional technique such as electroporation. Microorganisms having an antibiotic resistance are selected to isolate microorganisms having an inactivated galR gene.

Skilled artisans will recognize that the inactivated polynucleotide sequence of this invention can be generated by general cloning methods. For example, PCR amplification methods using oligonucleotide primers targeted to the galR gene can be used. Methods for PCR amplification are widely known in the art (see e.g. PCR Protocols: A Guide to Method and Application, Ed. M. Innis et al., Academic Press (1990)). The PCR comprises genomic DNA, suitable enzymes, primers, and buffers, and is conveniently carried out in a DNA Thermal Cycler (Perkin Elmer Cetus, Norwalk, Conn. USA). A positive PCR result is determined by, for example, detecting an appropriately-sized DNA fragment following agarose gel electrophoresis.

In an embodiment of the present invention, recombinant plasmids pT7blue/galR and pT7bluegalR::loxpKAN were prepared and an inactivated polynucleotide sequence ΔgalR::loxpKAN was obtained therefrom. Then, an *Escherichia coli* strain that is resistant to L-methionine, L-threonine and L-lysine analogues and α-aminobutyric acid and has a nutritional requirement for methionine and a leaky requirement for isoleucine, namely *Escherichia coli* Accession No. KCCM 10236; *Escherichia coli* FTR2717 having an inactivated pckA gene; *Escherichia coli* FTR8625 having inactivated pckA gene and aspA gene (Accession No. KCCM 10544); and *Escherichia coli* FTR7624 having an inactivated tyrR gene which regresses the expression of tyrB gene necessary for L-threonine biosynthesis (Accession No. KCCM 10538) were transformed with the inactivated polynucleotide sequence ΔgalR::loxpKAN by electroporation. As a result, the wild-type galR gene is inactivated to three types of novel strains capable of producing a higher concentration of L-threonine than the prototype strains. The novel strains were designated as *Escherichia coli* FTR2541, *Escherichia coli* FTR2537 and *Escherichia coli* FTR2533 and were deposited under the Budapest Treaty to the Korean Culture Center of Microorganisms on Dec. 4, 2003 and assigned Accession Nos. KCCM-10539, KCCM-10540 and KCCM-10541.

*Escherichia coli* FTR2541 was derived from *Escherichia coli* Accession No. KCCM 10236 which was derived from *Escherichia coli* TF4076. The *Escherichia coli* TF4076 (KFCC10718) requires methionine and has resistance to threonine. analogues (for example, α-amino-β-hydroxy valeric acid, AHV), lysine analogues (for example, S-(2-aminoethyl-L-cysteine, AEC), isoleucine analogues (for example, α-aminobutyric acid), methionine analogues (for example, ethionine) and the like. *Escherichia coli* Accession No. KCCM TF4076 is described in Korean Patent Publication No. 92-8365 which is incorporated herein in its entirety by reference. Phosphoenol pyruvate (PEP) is a precursor of oxaloacetate which is an intermediate of L-threonine biosynthesis pathway. The ppc gene and thr operon originated from the chromosomes of *Escherichia coli* Accession No. KCCM TF4076 were amplified by the PCR and were additionally integrated into the chromosomes of *Escherichia coli* Accession No. KCCM TF4076 to generate *Escherichia coli* Accession No. KCCM 10236. Thus, *Escherichia coli* Accession No. KCCM 10236 possesses two ppc genes and two threonine operons. *Escherichia coli* Accession No. KCCM 10236 is, therefore, capable of expressing higher levels of the ppc genes catalyzing the formation oxaloacetate from PEP and the enzymes necessary for threonine biosynthesis from aspartate (thrA: aspartokinase In-homoserine dehydrogenase, thrB: homoserine kinase, thrC: threonine synthase), thereby enabling an increase in L-threonine production. *Escherichia coli* FTR2537 was derived from *Escherichia coli* TFR8625 which was derived from *Escherichia coli* Accession No. KCCM 10236. pckA gene and aspA gene in a chromosome of *Escherichia coli* Accession No. KCCM 10236 were inactivated to improve L-threonine production. *Escherichia coli* FTR2533 was derived from *Escherichia coli* TFR7624 which was derived from *Escherichia coli* Accession No. KCCM 10236. tyrR gene in a chromosome of *Escherichia coli* Accession No. KCCM 10236 were inactivated to improve L-threonine production.

The present invention also provides a method of producing L-threonine, including: culturing the microorganism capable of producing L-threonine and having an inactivated galR gene; and isolating L-threonine from the culture.

In the production method of L-threonine, the culturing may be carried out in a suitable culture medium under suitable culturing conditions known in the art and may be readily adjusted according to the type of strain selected by those skilled in the art. The culturing may be carried out by batch operation, continuous operation, or fed-batch operation (see e.g. "Biochemical Engineering" by James M. Lee, Prentice-Hall International Editions, pp.138-176).

The culture medium should properly meet the requirements according to a stain selected. A variety of culture media are disclosed in literatures (see e.g. "Manual of Methods for General Bacteriology" by the American Society for Bacteriology, Washington D.C., USA, 1981). The culture medium contains carbon sources, nitrogen sources and trace amounts of ingredients. Examples of the carbon sources include carbohydrates such as glucose, sucrose, lactose, fructose, moltose, starch, cellulose; fats such as soybean oil, sunflower oil, castor oil, coconut oil; fatty acids such as palmitic acid, stearic acid, linoleic acid; alcohols such as glycerol and ethanol; and organic acids such as acetic acid. These carbon sources may be used alone or in combination. Examples of the nitrogen sources include organic substances such as peptone, yeast extract, meat extract, malt extract, corn steep liquor (CSL) and soybean meal; and inorganic substances such as urea, ammonium sulfate, ammonium chloride, ammonium phosphate, ammonium carbonate and ammonium nitrate. These nitrogen sources can be used alone or in combination. In the culture medium, phosphate sources such as potassium dihydrogenphosphate, dipotassium hydrogenphosphate, and corresponding sodium-containing salts can be included. Also, the culture medium can include metal salts such as magnesium sulfate or ferrous sulfate. In addition, amino acids, vitamins, and appropriate precursors can be included. The culture medium or precursor can be added to the culture in batch or continuous way.

Ammonium hydroxide, potassium hydroxide, ammonia, phosphate or sulfuric acid, etc. is appropriately added to the culture during culturing to adjust pH of the culture. Also, an antifoaming agent such as fatty acid polyglycol ester is added to the culture to prevent the formation of foam. Culturing is carried out under aerobic conditions by injecting oxygen or oxygen-containing gas (e.g. air) to the culture. The culturing temperature is in the range of 20 to 45° C., preferably 25 to 40° C. The culturing can be continued until the desired amount of L-threonine is obtained, preferably for 10 to 160 hours.

L-threonine can be isolated from the culture by ordinary methods known in the art. The isolation methods include centrifuging, filtration, ion exchange chromatography and crystallization, etc. For example, the supernatant obtained by centrifuging the culture at a low speed to remove biomass can be isolated through ion exchange chromatography.

Hereinafter, the present invention will be described more specifically by examples. However, the following examples are provided only for illustrations and thus the present invention is not limited to or by them.

EXAMPLES

Example 1

Construction of Recombinant Plasmid and Knock-out of galR Gene

In the present Example, a galR gene in a chromosome of *Escherichia coli* was knocked-out by homologous recombination. For this, a vector including a portion of the galR gene was prepared, and then was transformed into *Escherichia coli* host cell, followed by selecting strains having a knock-out galR gene.

Genomic DNA was extracted from L-threonine-producing *Escherichia coli* strain Accession No. KCCM 10236 by using the QIAGEN Genomic-tip System. The DNA fragment (about 850 bp) including ORF (open reading frame) of galR gene was amplified by PCR using the extracted genomic DNA as a template. The primers used were a pair of oligonucleotides (SEQ ID NO: 1 and SEQ ID NO: 2). PCR was performed by 30 cycles, each consisting of denaturation for 30 seconds at 94° C., annealing for 30 seconds at 60° C. and extension for 60 seconds at 72° C. in order.

The PCR product was loaded onto 1.0% agarose gel and subjected to electrophoresis. DNA was purified from the 856 bp galR gene band. The purified DNA was ligated to EcoRV site of cloning vector pT7Blue (Novagen Inc., USA) overnight at the temperature of 16° C. to construct the recombinant plasmid pT7Blue/galR (see FIG. 1). The resulting plasmid construct was transformed into *Escherichia coli* NM522. The transformed strain was plated on solid media containing 50 mg/L of carbenicillin and was cultured overnight at a temperature of 37° C.

Figure 2:
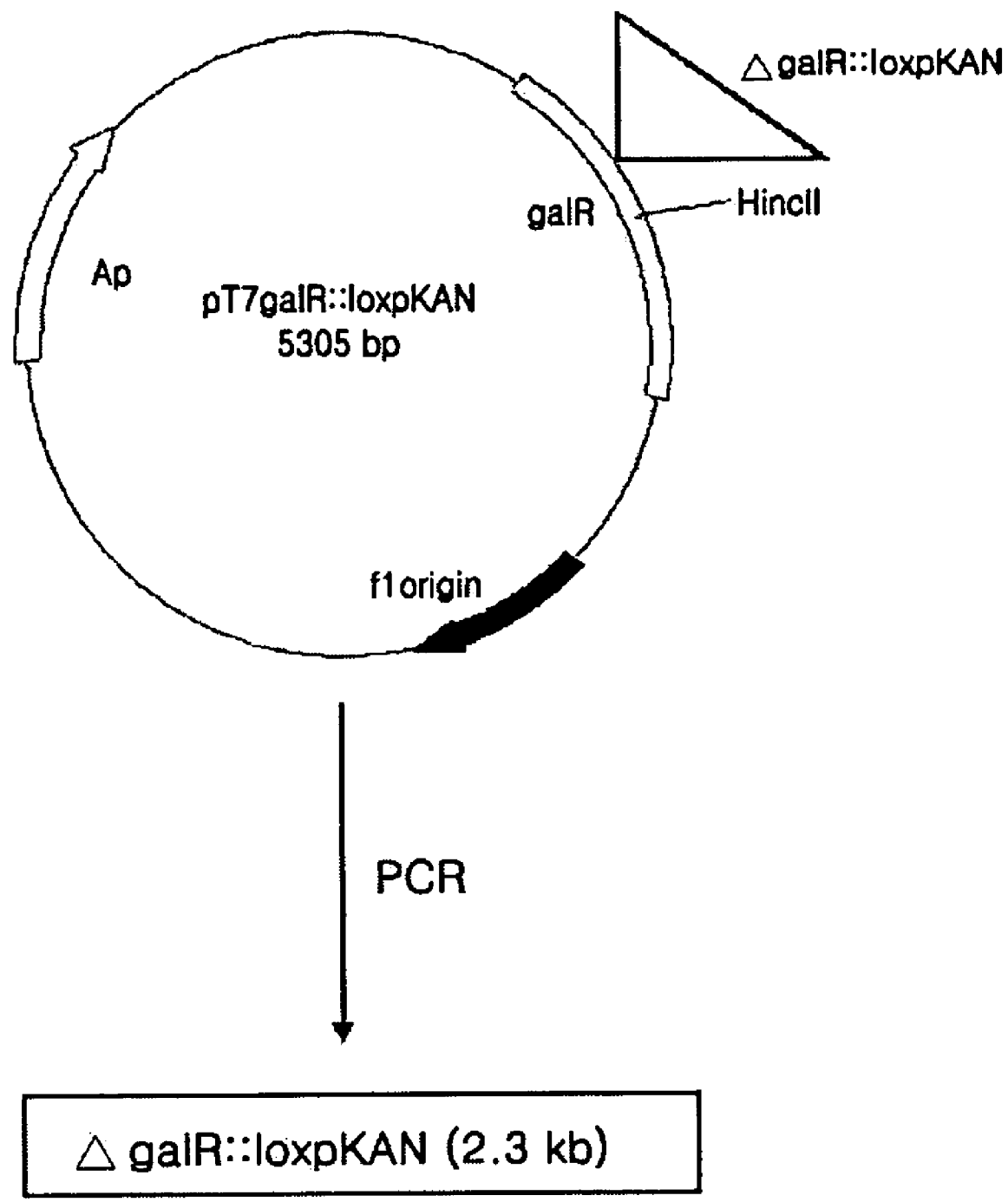
FIG. 2 depicts a construction of DNA fragment ΔgalR:: loxpKAN from recombinant plasmid pT7bluegalR::loxp-KAN.

The colonies formed were picked up with a platinum loop and inoculated into 3 ml of liquid LB media containing carbenicillin. After overnight culturing, plasmid DNAs were extracted from the culture using QIAGEN Mini Prep Kit. The plasmid DNA extract was digested with the restriction enzyme Mlu I and confirmed the cloning of galR gene. The confirmed plasmid pT7Blue/galR was cleaved with the restriction enzyme Hinc II and DNA was purified from a band of about 3.8 kb in 0.8% agarose gel. The purified DNA was blunt-ended by the treatment of Klenow enzyme. The resulting DNA fragment was blunt-end ligated with about 1.5 kb fragment of the gene for kanamycin resistance including loxp region, which was obtained by digesting plasmid pUG6 (U. Guldenre et al., Nucleic Acid Research 24 (13), 1996, pp 2519-2524) with Hinc II restriction enzyme and EcoRV, to construct about 5.3 kb recombinant plasmid pT7ΔgalR::loxpKAN (see FIG. 2).

*Escherichia coli* NM522 was transformed with the recombinant plasmid pT7ΔgalR::loxpKAN. The resulting transformant was streaked out onto a solid LB medium plate containing 50 mg/L of carbenicillin and 50 mg/L of kanamycin and cultured overnight at 32° C. The colonies formed were picked up with a platinum loop and inoculated into 3 ml of liquid LB media containing carbenicillin and kanamycin. After overnight culturing, plasmid DNAs were extracted using QIAGEN Mini Prep Kit. The DNA fragment (about 2.3 kb) including ORF of galR gene and loxpKAN site was amplified by PCR using the extracted plasmid DNA as a template. The primers used were a pair of oligonucleotides (SEQ ID NO: 1 and SEQ ID NO: 2). PCR was performed by 30 cycles, each consisting of denaturation for 30 seconds at 94° C., annealing for 30 seconds at 60° C. and extension for 60 seconds at 72° C. in order.

The resulting DNA fragment ΔgalR::loxpKAN was transformed into L-threonine-producing *Escherichia coli* strain Accession No. KCCM 10236, *Escherichia coli* FTR8625 and *Escherichia coli* FTR7624 by electroporation and the resulting transformant was streaked out onto a solid LB medium containing kanamycin to select colonies having a knock-out galR gene. The selected colonies were tested for their production of L-threonine in flask cultures.

Example 2

L-threonine Production in Erlenmeyer Flask by Selected Strains

Thirty colonies selected in Example 1 were cultured in an Erlenmeyer flask containing the threonine titration medium given in Table 1 below, and L-threonine production was compared.

TABLE 1

Threonine titration medium

| Ingredients | Concentration (per liter) |
|---|---|
| Glucose | 70 g |
| Ammonium sulfate | 28 g |
| $KH_2PO_4$ | 1.0 g |
| $MgSO_4.7H_2O$ | 0.5 g |
| $FeSO_4.7H_2O$ | 5 mg |
| $MnSO_4.8H_2O$ | 5 mg |
| Calcium carbonate | 30 g |
| L-methionine | 0.15 g |
| Yeast extract | 2 g |
| pH 7.0 | |

Each colony was cultured overnight on LB solid medium in a incubator at 32° C. Then, one platinum loop of the culture was inoculated into 25 ml of the titration medium and cultured at 32° C. and 250 rpm for 42 to 48 hours.

L-threonine from the culture was analyzed by high performance liquid chromatography (HPLC). The analysis results are given in Table 2 below. It can be seen from the results that the prototype strain Accession No. KCCM 10236 produces 23 g/L L-threonine for 48 hours and *Escherichia coli* FTR2541 of the present invention in which galR gene has been knocked out produces 25 g/L L-threonine for 44 hours. Prototype strains *Escherichia coli* FTR8625 and FTR7624 produce 26 g/L L-threonine for 48 hours and *Escherichia coli* FTR2537 and FTR2533 of the present invention in which galR gene has been knocked out produces 28 g/L L-threonine for 44 hours and 42 hours, respectively. Therefore, it was observed that the present transformed microorganisms improve fermentation time and concentration of L-threonine up to about 7-9% and increase the output of L-threonine up to about 18-25% in comparison to the prototype strains. The selected *Escherichia coli* FTR2541, *Escherichia coli* FTR2537 and *Escherichia coli* FTR2533 were deposited to the Korean Culture Center of Microorganisms on Dec. 4, 2003 and assigned Accession Nos. KCCM-10539, KCCM-10540 and KCCM-10541. Also, the prototype strains *Escherichia coli* FTR8625 and *Escherichia coli* FTR7624 were deposited to the Korean Culture Center of Microorganisms on Dec. 4, 2003 and assigned Accession Nos. KCCM-10544 and KCCM-10538.

TABLE 2

Flask titration test results of strains

| | Strains | | | | | |
|---|---|---|---|---|---|---|
| | KCCM10236 | FTR2541 (KCCM10539) | FTR8625 (KCCM10544) | FTR2537 (KCCM10540) | FTR7624 (KCCM10538) | FTR2533 (KCCM10541) |
| L-threonine (g/L) | 23 | 25 | 26 | 28 | 26 | 28 |
| Time (hr) | 48 | 44 | 48 | 44 | 48 | 42 |
| Output (g/L/hr) | 0.48 | 0.57 | 0.54 | 0.64 | 0.54 | 0.67 |

As demonstrated by Examples, the ability to biosynthesizing L-threonine of microorganisms is improved by knock-out of galR gene. This is probably because expression of the galP gene is increased by the knock-out of the galR gene, thereby increasing the supply rate of saccharide to the inside of strain, which increases the specific growth rate of L-threonine-producing strains. However, the improvement in productivity of the microorganism is not based on only this mechanism.

As described above, the microorganism having an inactivated galR gene of the present invention can produce L-threonine by fermentation in high yield.

Also, according to the method of producing the microorganism, the microorganism capable of producing L-threonine in high yield can be produced.

Also, according to the method of producing L-threonine of the present invention, high yield of L-threonine can be produced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microorganism capable of producing L-threonine and having an inactivated galR gene wherein said microorganism is *Escherichia coli* which is selected from the group consisting of *Escherichia coli* FTR2541 (KCCM-10539), *Escherichia coli* FTR2537 (KCCM-10540) and *Escherichia coli* FTR2533 (KCCM-10541).

2. A method for producing L-threonine comprising: culturing the *Escherichia coli* of claim 1 and isolating L-threonine from the culture.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
ctcccgacac gctcaaccca gatt                                              24

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tgcccgccag aaaaagtcag c                                                 21
```